United States Patent
Oguri et al.

(10) Patent No.: US 7,402,702 B2
(45) Date of Patent: Jul. 22, 2008

(54) PROCESS FOR PRODUCING TERTIARY AMINE

(75) Inventors: Shinji Oguri, Wakayama (JP); Toru Nishimura, Wakayama (JP)

(73) Assignee: Kao Corporation, Tokyo (JP)

( * ) Notice: Subject to any disclaimer, the term of this patent is extended or adjusted under 35 U.S.C. 154(b) by 244 days.

(21) Appl. No.: 11/289,476

(22) Filed: Nov. 30, 2005

(65) Prior Publication Data

US 2006/0135815 A1 Jun. 22, 2006

(30) Foreign Application Priority Data

Dec. 9, 2004 (JP) ............................. 2004-356698

(51) Int. Cl.
*C07C 209/14* (2006.01)
*C07C 209/16* (2006.01)
*C07C 209/18* (2006.01)

(52) U.S. Cl. ...................................... 564/479; 564/480

(58) Field of Classification Search ....................... None
See application file for complete search history.

(56) References Cited

U.S. PATENT DOCUMENTS

2006/0135815 A1 6/2006 Oguri et al.

FOREIGN PATENT DOCUMENTS

JP 2001-151733 6/2001

OTHER PUBLICATIONS

"Kagaku Kogaku Binran", Chemical Engineering Handbook, revised 5$^{th}$ edition, Apr. 15, 1992, pp. 901-902, with partial English translation.
U.S. Appl. No. 11/911,032, filed Oct. 9, 2007, Nishimura, et al.

*Primary Examiner*—Brian J Davis
(74) *Attorney, Agent, or Firm*—Oblon, Spivak, McClelland, Maier & Neustadt, P.C.

(57) ABSTRACT

The invention relates to a process for producing a tertiary amine, which includes reacting an alcohol with a primary or secondary amine gas in the presence of a catalyst with an agitating vessel under the stirring conditions where the ratio $(P_g/P_0)$ of agitating power at the time of the maximum flow rate of an introducing gas ($P_g$ [W]) to agitating power at the time of no introduction of the gas ($P_0$ [W]) becomes $10^{-1.8 N_a}$ or more wherein $N_a$ is the gas flow number, and $N_a = Q_g/nd^3$ whereupon $Q_g$ [m$^3$/s] is the flow rate of an introducing gas, n [1/s] is the number of revolutions, and d [m] is the diameter of an agitating impeller.

6 Claims, 2 Drawing Sheets

US 7,402,702 B2

PROCESS FOR PRODUCING TERTIARY AMINE

FIELD OF THE INVENTION

The present invention relates to a process for producing a tertiary amine from an alcohol and a primary or secondary amine gas in the presence of a catalyst.

BACKGROUND OF THE INVENTION

In the field of production of tertiary amines, side products such as monomethyl dialkylamine are formed particularly in production of dimethyl monoalkylamine by reacting an alcohol with dimethylamine in the presence of a catalyst, thus causing a reduction in yield. To solve this problem, JP-A 2001-151733 for example discloses a process for producing a tertiary amine at a high yield by suppressing side products with a combination of a catalyst and specific reaction conditions.

In the conventional techniques such as those described above, those skilled in the art have produced tertiary amines under general stirring conditions in this field. That is, a correlation of the gas flow number ($N_A$) and agitating power ratio ($P_g/P_0$), which indicates a mixed state of liquid and gas, is disclosed in FIG. 20-14 on page 902 in "Kagaku Kogaku Binran" (Chemical Engineering Handbook), revised 5th edition, published on Apr. 15, 1992, pp. 901-902 and edited by The Society of Chemical Engineers, Japan (SCE). There is also a disclosure wherein the agitating power ratio is practically 0.6 or more.

SUMMARY OF THE INVENTION

The present invention relates to a process for producing a tertiary amine, which includes producing a tertiary amine by reacting an alcohol with a primary or secondary amine gas in the presence of a catalyst with an agitating vessel under stirring conditions where the ratio ($P_g/P_0$) of agitating power at the time of the maximum flow rate of an introducing gas ($P_g$ [W]) to agitating power at the time of no introduction of gas ($P_0$ [W]) becomes $10^{-1.8 Na}$ or more, wherein $N_a$ is the gas flow number, and $N_a = Q_g/nd^3$ whereupon $Q_g$ [m$^3$/s] is the flow rate of introducing gas, n [1/s] is the number of revolutions, and d [m] is the diameter of an agitating impeller.

Figure 1:
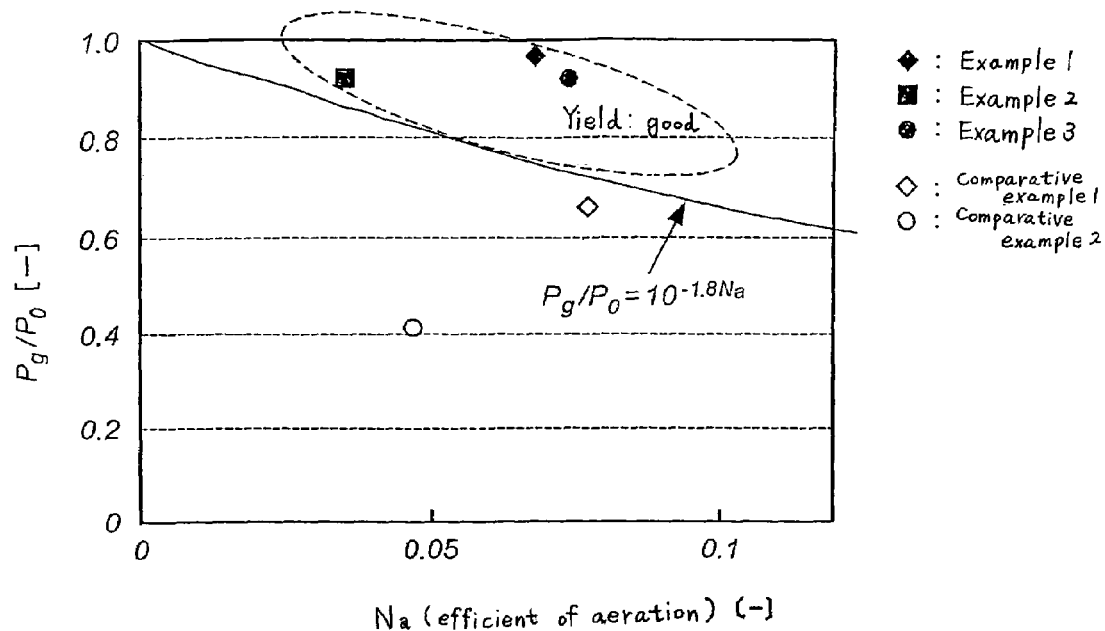
FIG. 1 is a graph showing the relationship between the gas flow number $N_a$ and the agitating power ratio ($P_g/P_0$).

1: concave turbine.

11: edged turbine.

DETAILED DESCRIPTION OF THE INVENTION

A standard 6-blade disk turbine used frequently in this field is inefficient when the amount of introducing gas is relatively high because the number of stirring revolutions and/or the diameter of an agitating impeller should be increased to reduce the gas flow number and to improve the agitating power ratio.

The present invention provides a process for producing a tertiary amine at a high yield by reacting an alcohol with a primary or secondary amine gas in the presence of a catalyst.

According to the present invention, the intended tertiary amine can be effectively obtained at a high yield of production.

In the present invention, the starting alcohol used in production of the tertiary amine is preferably a linear or branched C6 to C36 saturated or unsaturated aliphatic alcohol, and examples thereof include hexyl alcohol, octyl alcohol, lauryl alcohol, myristyl alcohol, stearyl alcohol, behenyl alcohol and oleyl alcohol, a mixed alcohol thereof, Ziegler alcohol obtained by the Ziegler process, an oxo alcohol obtained by an oxo process, and Guerbet alcohol.

The starting primary or secondary amine used in production of the tertiary amine is preferably an aliphatic primary or secondary amine, and examples thereof include methylamine, dimethylamine, ethylamine, diethylamine, dodecylamine, didodecylamine etc.

The alcohol and primary or secondary amine used as the starting materials give the corresponding tertiary amine wherein a hydrogen atom bound to the nitrogen atom of the primary or secondary amine has been replaced by an alkyl group and/or an alkenyl group derived from the alcohol. For example, the tertiary amine obtained from dodecyl alcohol and dimethylamine is N-dodecyl-N,N-dimethylamine which is distinguished from tertiary-amine side products N,N-didodecyl-N-methylamine and N,N,N-tridodecylamine generated by disproportination of dimethylamine.

As the catalyst used in the present invention, known catalysts can be used, and particularly a Cu-type metal can be preferably used. For example, Cu alone or a metal of two, three or more components consisting of Cu plus a transition metal element such as Cr, Co, Ni, Fe or Mn can be mentioned. Further, catalysts containing these metal elements carried on silica, alumina, titania or zeolite and the like can also be mentioned.

In the present invention, a catalyst which has been reduced separately in advance with hydrogen gas or the like may be used. It is preferable that the catalyst is reduced with hydrogen gas while the hydrogen gas is being introduced into the reaction system.

The reaction in the present invention is carried out in an agitating vessel under stirring conditions where the ratio ($P_g/P_0$) of agitating power at the time of the maximum flow rate of introducing gas, that is, the maximum flow rate of a primary or secondary amine gas and a hydrogen gas in total to agitating power at the time of no introduction of gas becomes $10^{-1.8 Na}$ or more. In the present invention, the pressure in the system is desirably not significantly higher than normal pressures. The reaction temperature varies depending on the type of the catalyst, but the reaction is carried out preferably at a temperature of 100 to 250° C.

The flow rate of a primary or secondary amine gas is regulated such that the amount of the primary or secondary amine gas in exhaust gas (excluding formed water) to be discharged into the outside of the reaction system is 0.5 to 50 vol % (relative to the exhaust gas), preferably 5 to 30 vol %, more preferably 10 to 30 vol %, in order to maintain the reaction activity and to suppress the disproportionation of primary or secondary amine causing the side reaction described above. The flow rate of the hydrogen gas is preferably 1 to 100 cm$^3$/hr, more preferably 10 to 50 cm$^3$/hr, per g of the starting alcohol.

The present inventors, when produced a tertiary amine under various stirring conditions, found that whether yield is good or not can be judged by the agitating power ratio ($P_g/P_0$) depending on the gas flow number $N_a$ as shown in FIG. 1, that is, they found that there is a critical value of stirring conditions for efficiently producing the tertiary amine. According to the desirable flow rate of the introducing primary or secondary amine gas as described above, the flow rate of the introducing gas should be the greatest at an initial stage of the reaction and then decreased as the reaction proceeds. The present inventors found that the desired results can be achieved by carrying out the reaction at least under stirring conditions where the ratio ($P_g/P_0$) of agitating power at the time of the maximum flow rate of the introducing gas ($P_g$ [W]) to agitating power at the time of no introduction of the gas ($P_0$ [W]) becomes $10^{-1.8Na}$ or more.

The critical value of $10^{-1.8Na}$ for agitating power ratio was derived from the results in FIG. 1, on the basis of the following relationship (1) between the gas flow number and agitating power ratio with a standard 6-disk turbine, disclosed on page 902 in "Kagaku Kogaku Binran" (Chemical Engineering Handbook) supra.

$$\log_{10} \frac{P_g}{P_0} = -192 \left(\frac{d}{D}\right)^{4.38} \left(\frac{d^2 n \rho_c}{\eta_c}\right)^{0.115} \left(\frac{dn^2}{g}\right)^{1.96(d/D)} N_a \quad (1)$$

wherein $P_g$ [W] is agitating power during gas introduction; $P_0$ [W], agitating power during no gas introduction; d [m], the diameter of an agitating impeller; D [m], the diameter of an agitating vessel (inner diameter); n [1/s], the number of stirring revolutions; $\rho_c$ [kg/m$^3$], liquid density; $\eta_c$ [Pa·s], liquid viscosity; g [m/s$^2$], acceleration of gravity; $N_a$ [–], the gas flow number (=$Q_g$/nd$^3$ where $Q_g$ [m$^3$/s] is the flow rate of a primary or secondary amine gas and a hydrogen gas).

That is, the critical equation for agitating power ratio for judging whether yield is good or not can be expressed in the following equation (2) from the equation (1).

$$\log_{10} \frac{P_g}{P_0} = KN_a \quad (2)$$

wherein K [–] is a constant.

The value of K in the equation (2) as determined from FIG. 1 is –1.8, and the equation (2) can be expressed as the following equation (3):

$$(P_g/P_0) = 10^{-1.8Na} \quad (3)$$

The desired product can be obtained at a high yield by continuing the reaction under the stirring conditions where the ratio ($P_g/P_0$) of agitating power at the time of the maximum flow rate of an introducing gas ($P_g$ [W]) to agitating power at the time of no introduction of the gas ($P_0$ [W]) becomes the value of the equation (3) or larger.

The agitating vessel used in the present invention is composed of a tank (vessel) equipped with a heating unit, an introducing tube (sparger) for introducing a starting amine gas and a hydrogen gas into the vessel, and an agitator equipped with an agitating impeller.

As the heating unit, a known unit can be used, and for example, a heating unit having a heating medium introducing through an internal coil or in a jacket, or an electric heater, can be mentioned. Desirably, the heating unit has a temperature regulating function for regulating the temperature of a liquid in the vessel.

As the introducing tube (sparger) for introducing a gas, a known sparger can be utilized, and for dispersing the introduced gas into a liquid, a single tube-type sparger having a pipe below the position of an agitating impeller in the bottom of the vessel, a sparger having a large number of gas-jetting holes formed on a pipe, and a sparger of ring type having gas-jetting holes arranged circumferentially is preferably used.

Figure 2:
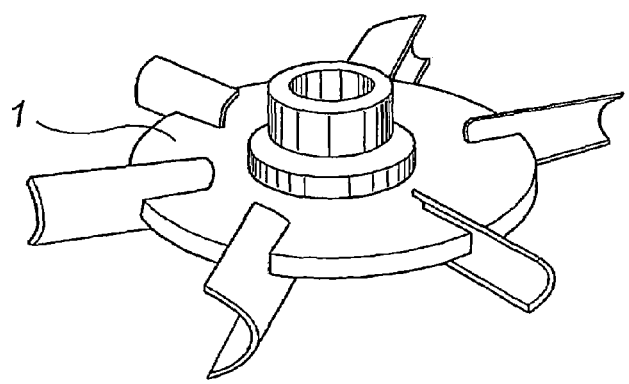
FIG. 2 is a perspective view showing an example of the concave turbine used in the present invention.
Figure 3:
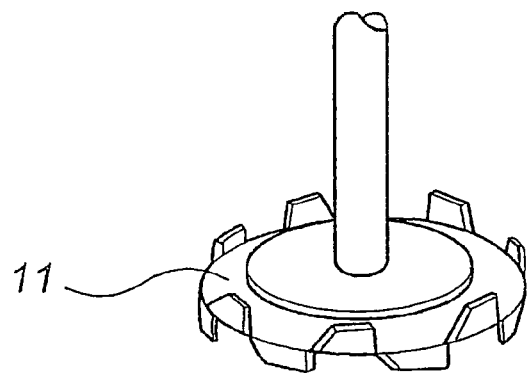
FIG. 3 is a perspective view showing an example of the edged turbine used in the present invention.
Figure 4:
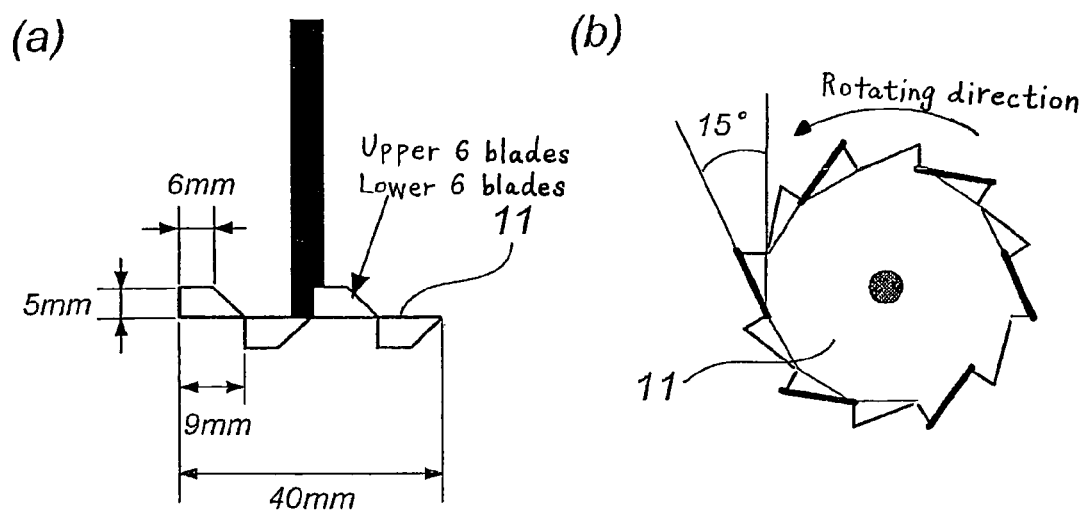
FIG. 4 is a view showing an example of the edged turbine used in the present invention, wherein (a) is a front view, and (b) is a plan view.

Generally, stirring conditions include various factors, and the type of an agitating impeller, the diameter of the agitating impeller, and the number of revolutions, particularly the type of the agitating impeller, are important for carrying out the reaction in the present invention under the stirring condition where $P_g/P_0$ becomes $10^{-1.8Na}$ or more. The agitating impeller used preferably in the present invention includes a shear-force type agitating impeller. The shear-force type agitating impeller, herein used, means an agitating impeller having a higher shear power than the jetting-out power thereof. The shear-force type agitating impeller includes a concave turbine and an edged turbine. The concave turbine is defined in U.S. Pat. No. 5,791,780 etc. It is an agitating impeller 1 as shown in FIG. 2, and for example SRGT manufactured by Scaba is mentioned. The edged turbine has blades attached at an almost right angle to a disk and arranged at an angle of 0 to 30° relative to the circumferential direction, which is specifically an agitating impeller 11 shown in FIGS. 3 and 4.

The agitating impeller diameter (d [m]) is determined such that the ratio (d/D) thereof to the vessel diameter (D [m]) becomes preferably 0.15 to 0.45, more preferably 0.2 to 0.4. Depending on the vessel diameter (size of the agitating vessel), a plurality of agitating impellers can be arranged in multiple stages. In this case, the agitating impeller described above is arranged so as to be positioned above the sparger, thus allowing a gas introduced from the sparger to be dispersed in the liquid, while in an upper stage, axial flow agitating impellers causing a liquid stream to prevent sedimentation of a catalyst, such as a marine propeller and a pitched paddle, are desirably arranged. When the agitating machine has a plurality of agitating impellers, the agitating power ($P_g$ [W]) at the time of the maximum flow rate of introducing gas or the agitating power ($P_0$ [W]) at the time of no introduction of the gas is the agitating power of the agitating machine as a whole.

After the type and the diameter of the agitating impeller are determined, the number of stirring revolutions is determined desirably such that $P_g/P_0$ becomes $10^{-1.8Na}$ or more. When the number of stirring revolutions is regulated such that $P_g/P_0$ becomes $10^{-1.8Na}$ or more, the number of stirring revolutions at an initial stage of the reaction is established to be preferably the maximum. When the number of stirring revolutions is regulated, the agitating machine should be equipped with a speed changer or an inverter, but in the present invention, the agitating impeller described above can be suitably selected to achieve an always constant (fixed) number of stirring revolutions, and thus there is an advantage that an additional device such as a speed changer or an inverter is not necessary.

EXAMPLES

Hereinafter, the present invention is described by reference to the Examples. The Examples are set forth for mere illustration of the present invention and not intended to limit the present invention.

Example 1

A 2-L separable flask equipped with a baffle was charged with 1200 g dodecyl alcohol (Kalcol 2098 manufactured by Kao Corporation) and 2 g (0.17 wt % relative to the starting alcohol) of acatalyst described in Example 1 in JP-B 3-4534, and heating was initiated under stirring at a revolution number of 275 rpm with a concave turbine having a blade diameter of 50 mm. A hydrogen gas was introduced at a flow rate of 33 NL/hr into the system to activate the catalyst by reduction. Thereafter, while the flow rate of the hydrogen gas was maintained, introducing of dimethylamine gas was initiated, and the flow rate of the dimethylamine gas was gradually increased such that the flow rate became 109 NL/hr when 220° C. was reached, and the reaction was initiated where the point in time when 220° C. was reached was regarded as 0 hour of the reaction. The reaction pressure was normal pressure, and water formed by the reaction and an excess of dimethylamine gas and hydrogen gas were introduced through a rectification column, separated from the unreacted alcohol and the tertiary amine, and discharged to the outside of the reaction system. During the reaction, the number of revolutions, the temperature in the system and the flow rate of hydrogen gas were maintained, while the flow rate of dimethylamine gas was regulated such that the proportion of dimethylamine in the exhaust gas excluding the formed water became 5 to 30 vol %. The reaction was monitored by gas chromatography, and when the unreacted alcohol was reduced to 1% or less, introduction of dimethylamine gas was terminated, and only hydrogen was introduced for 0.5 hour. The yield (excluding side products) and the elapsed time (reaction time) from the initiation of the reaction at the time of 1% unreacted alcohol, as determined from data in gas chromatography, are shown in Table 1. $P_g/P_0$ at the time of the maximum flow rate of the introducing gas is shown in FIG. 1.

Example 2

Table 1 shows the yield (excluding side products) and the elapsed time (reaction time) from the initiation of the reaction at the time of 1% unreacted alcohol, where a tertiary amine was produced in the same manner as in Example 1 except that the number of stirring revolutions was changed to 530 rpm. $P_g/P_0$ at the time of the maximum flow rate of the introducing gas is shown in FIG. 1.

Example 3

Table 1 shows the yield (excluding side products) and the elapsed time (reaction time) from the initiation of the reaction at the time of 1% unreacted alcohol, where a tertiary amine was produced in the same manner as in Example 1 except that the number of stirring revolutions was changed to 600 rpm with an edged turbine having a blade diameter of 37.5 mm as an agitating impeller. $P_g/P_0$ at the time of the maximum flow rate of the introducing gas is shown in FIG. 1.

Comparative Example 1

Table 1 shows the yield (excluding side products) and the elapsed time (reaction time) from the initiation of the reaction at the time of 1% unreacted alcohol, where a tertiary amine was produced in the same manner as in Example 1 except that the number of stirring revolutions was changed to 275 rpm with a flat turbine having a blade diameter of 48 mm as an agitating impeller. $P_g/P_0$ at the time of the maximum flow rate of the introducing gas is shown in FIG. 1.

Comparative Example 2

Table 1 shows the yield (excluding side products) and the elapsed time (reaction time) from the initiation of the reaction at the time of 1% unreacted alcohol, when a tertiary amine was produced in the same manner as in Example 1 except that the number of stirring revolutions was changed to 400 rpm with a marine propeller having a blade diameter of 50 mm as an agitating impeller. $P_g/P_0$ at the time of the maximum flow rate of the introducing gas is shown in FIG. 1.

TABLE 1

|  |  |  | Example | | | Comparative example | |
|---|---|---|---|---|---|---|---|
|  |  |  | 1 | 2 | 3 | 1 | 2 |
| Amount of alcohol charged (Dodecyl alcohol) |  | [kg] | 1.2 | | | 1.2 | |
| Amount of catalyst |  | [wt %] | 0.17 | | | 0.17 | |
| Flow rate of gas | Dimethyl amine | [NL/Hr] | 109 | | | 109 | |
|  |  |  | (at the time of the maximum flow rate) | | | (at the time of the maximum flow rate) | |
|  | Hydrogen | [NL/Hr] | 33 | | | 33 | |
| Reaction temperature |  | [° C.] | 220 | | | 220 | |
| Stirring conditions | Blade type |  | Concave turbine | Edged turbine | | Flat turbine | Marine Propeller |
|  | Blade diameter | [m] | 0.05 | | 0.0375 | 0.048 | 0.05 |
|  | Number of revolutions | [r/min] | 275 | 530 | 600 | 275 | 400 |
| Gas flow number | $N_a$ (at the time of the maximum flow rate of gas) | [—] | 0.069 | 0.036 | 0.075 | 0.078 | 0.047 |
| Agitating power ratio | $P_g/P_0$ (determined value) | [—] | 0.96 | 0.92 | 0.92 | 0.66 | 0.41 |
|  | $P_g/P_0$ (critical value*[1]) | [—] | 0.75 | 0.86 | 0.73 | 0.73 | 0.82 |
| Reaction time*[2] |  | [Hr] | 4.9 | 4.5 | 4.5 | 5.5 | 5.5 |
| Yield*[3] |  | [%] | 95.5 | 95.1 | 95.2 | 93.5 | 95.1 |

*[1]Critical value of agitating power ratio obtained by substituting $N_a$ in the equation (3).
*[2]Reaction time for unreacted alcohol to be reduced to 1%.
*[3]Yield of the product at the time of 1% unreacted alcohol.

The invention claimed is:

1. A process for producing a tertiary amine, which comprises reacting an alcohol with a primary or secondary amine gas in the presence of a catalyst with an agitating vessel under the stirring conditions where the ratio ($P_g/P_0$) of agitating power at the time of the maximum flow rate of an introducing gas ($P_g$ [W]) to agitating power at the time of no introduction of the gas ($P_0$ [W]) becomes $10^{-1.8Na}$ or more wherein $N_a$ is the gas flow number, and $Na=Q_g/nd^3$ whereupon $Q_g$ [m³/s] is the flow rate of an introducing gas, n[1/s] is the number of revolutions, and d [m] is the diameter of an agitating impeller, wherein the agitation is carried out with a shear-force agitating impeller, and wherein the catalyst comprises a metal which is Cu alone or combined with at least one transition metal element.

2. The process for producing a tertiary amine according to claim 1, wherein the alcohol is a linear or branched C6 to C36 saturated or unsaturated aliphatic alcohol.

3. The process for producing a tertiary amine according to claim 1, wherein the primary or secondary amine is an aliphatic primary or secondary amine.

4. The process for producing a tertiary amine according to claim 1, wherein the shear-force agitating impeller is a concave turbine or an edged turbine.

5. The process for producing a tertiary amine according to claim 2, wherein the primary or secondary amine is an aliphatic primary or secondary amine.

6. The process for producing a tertiary amine according to claim 1, wherein the alcohol is dodecyl alcohol and the primary or secondary amine is dimethyl amine.

* * * * *